United States Patent
Zhou et al.

(10) Patent No.: US 9,089,701 B2
(45) Date of Patent: Jul. 28, 2015

(54) TECHNIQUES AND FUNCTIONAL ELECTRICAL STIMULATION TO ELIMINATE DISCOMFORT DURING ELECTRICAL STIMULATION OF THE RETINA

(75) Inventors: Chunhong Zhou, Oceanside, CA (US); Avraham I. Caspi, La Jolla, CA (US); Kelly H. McClure, Simi Valley, CA (US); Matthew J. McMahon, Washington, DC (US); Arup Roy, Valencia, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1198 days.

(21) Appl. No.: 12/562,022

(22) Filed: Sep. 17, 2009

(65) Prior Publication Data
US 2010/0087895 A1    Apr. 8, 2010

Related U.S. Application Data

(60) Provisional application No. 61/097,968, filed on Sep. 18, 2008.

(51) Int. Cl.
*A61N 1/00* (2006.01)
*A61N 1/36* (2006.01)
*A61N 1/05* (2006.01)

(52) U.S. Cl.
CPC ........... *A61N 1/36046* (2013.01); *A61N 1/0543* (2013.01)

(58) Field of Classification Search
CPC .................. A61N 1/36046; A61N 1/0543
USPC .................................... 600/558; 607/53–54
See application file for complete search history.

(56) References Cited

U.S. PATENT DOCUMENTS

| 5,109,844 | A | 5/1992 | de Juan, Jr. et al. |
| 5,935,155 | A | 8/1999 | Humayun et al. |
| 6,400,989 | B1 | 6/2002 | Eckmiller |
| 6,458,157 | B1 | 10/2002 | Suaning |

(Continued)

FOREIGN PATENT DOCUMENTS

| WO | WO2007/149291 | 12/2007 |
| WO | WO2008/140980 | 11/2008 |

*Primary Examiner* — Catherine Voorhees
*Assistant Examiner* — Roland Dinga
(74) *Attorney, Agent, or Firm* — Scott B. Dunbar

(57) ABSTRACT

Techniques and functional electrical stimulation to eliminate discomfort during electrical stimulation of the retina are provided. According to a first technique, discomfort is eliminated through control of timing group assignment. According to a second technique, discomfort is eliminated through an edge detection method. According to a third technique, brightness clipping is used to eliminate discomfort. According to a fourth technique, direct reduction of current is obtained by scaling it down by a factor which is dependent on the sum of current in all electrodes. According to a fifth technique, the current being fed to each electrode is adjusted, by dividing it by a weighted sum of currents fed to the surrounding electrodes. According to a sixth technique, a method based on the current summation effect is used. According to a seventh technique, a large return electrode is used. According to an eighth technique, the return electrode is used for a pseudo-multi-polar stimulation.

6 Claims, 9 Drawing Sheets

(56) References Cited

U.S. PATENT DOCUMENTS

| | | | |
|---|---|---|---|
| 2002/0010496 A1* | 1/2002 | Greenberg et al. | 607/54 |
| 2002/0038134 A1 | 3/2002 | Greenberg et al. | |
| 2006/0184062 A1* | 8/2006 | Greenberg et al. | 600/558 |
| 2006/0184245 A1* | 8/2006 | Graf et al. | 623/6.63 |
| 2007/0073358 A1* | 3/2007 | Greenberg et al. | 607/54 |
| 2007/0255343 A1* | 11/2007 | McMahon et al. | 607/54 |
| 2008/0294225 A1* | 11/2008 | Roy et al. | 607/54 |
| 2010/0057166 A1* | 3/2010 | Ahuja et al. | 607/53 |

* cited by examiner

AMPLITUDE A4 > A3 > A2 > A1

TECHNIQUES AND FUNCTIONAL ELECTRICAL STIMULATION TO ELIMINATE DISCOMFORT DURING ELECTRICAL STIMULATION OF THE RETINA

CROSS REFERENCE TO RELATED APPLICATIONS

The present application claims priority to U.S. Provisional Application 61/097,968 filed on Sep. 18, 2008 and incorporated herein by reference in its entirety.

FIELD

The present disclosure relates to discomfort elimination during electrical stimulation. In particular, it relates to techniques and functional electrical stimulation to eliminate discomfort during electrical stimulation of the retina.

BACKGROUND

Systems for the electrical stimulation of the retina by a retinal electrode array held against the retina are known. See, for example, U.S. Pat. No. 5,935,155, incorporated herein by reference in its entirety, where a system for capturing a video image, transferring the image wirelessly into a living body and applying the image to a retinal electrode array is shown.

During video stimulation, subjects often report unpleasantly high brightness, or physical discomfort, when the camera input is very bright (the video levels are high throughout the entire image and discomfort can be felt also on single electrodes). Therefore, there is a need to avoid discomfort while maintaining a bright percept from stimulation.

Additionally, when multiple electrodes on the retinal implant are stimulating at the same time, e.g., when presenting a pattern to the subject, electric charges often interact with each other and create a much brighter pattern than intended. Therefore, also in this case, there is a need to compensate for the interactions, so that images or patterns can be presented with more consistent contrast and brightness and also eliminate discomfort.

SUMMARY

According to a first aspect, a method for assigning image pixels of a digital image to electrodes of a visual prosthesis is provided, the electrodes adapted to provide electrical signals to a patient according to a temporal stimulation pattern, the temporal stimulation pattern defining one or more timing groups of electrodes, the method comprising: a) selecting the brightest pixels of the digital image; b) spreading said brightest pixels across the one or more timing groups; and c) repeating a) and b) for the remaining pixels of the image, until all pixels have been assigned to said one or more timing groups.

According to a second aspect, a digital image edge detection method for a patient wearing a visual prosthesis is provided, the method comprising one or more steps, wherein at each step the following operations are performed to collect pixels for presentation to the patient: a) determining a threshold to separate edge pixels from non-edge pixels, thus detecting a set of edge pixels; b) computing a total current value corresponding to a brightness sum value of i) the edge pixels determined in a) and ii) the edge pixels for presentation collected so far; c) if the total current value is less than a discomfort current value for the patient wearing the visual prosthesis, adding the set of edge pixels to the pixels for presentation to the patient and performing a further operation by repeating a), b) and c), otherwise terminating the detection method; and d) presenting to the patient the pixels collected for presentation.

According to a third aspect, a method for stimulating current to a patient wearing a visual prosthesis is provided, the visual prosthesis comprising a plurality of electrodes adapted to stimulate the patient with the current, the method comprising: providing current stimulation amplitudes for each electrode, each amplitude corresponding to brightness of an image pixel to be presented to the patient; providing an input current stimulation limit, the limit corresponding to a discomfort limit for the patient; selecting a current clipping level to saturate current stimulation amplitudes higher than the current clipping level to the current clipping level; calculating a total stimulation current of the electrodes based on the current clipping level; if the total stimulation current is less than the input current stimulation limit, increasing the current clipping level and calculating the total stimulation current of the electrodes based on the increased current clipping level, and repeating increase of the current clipping level until a distance between the input current stimulation limit and the total stimulation current of the electrodes is minimized, thus finding the current clipping level to be adopted for stimulation.

According to a fourth aspect, a method for reducing discomfort to a patient wearing a visual prosthesis is provided, the visual prosthesis comprising a plurality of electrodes adapted to stimulate the patient with current, wherein the amount of current to be provided by each electrode is indicative of brightness of an image area associated to said each electrode, the method comprising: scaling the amount of current to be provided by said each electrode according to a scaling factor, the scaling factor depending on the sum of the amount of current to be provided by all electrodes.

According to a fifth aspect, a method for compensating interactions among electrodes of a retinal stimulator is provided, the electrodes adapted to being fed with current corresponding to brightness levels, in order to present an image or pattern having consistent contrast and brightness to a patient wearing the retinal stimulator, the method comprising: adjusting the current being fed to each electrode, by dividing said current by a weighted sum of currents fed to electrodes surrounding said each electrode.

According to a sixth aspect, a stimulation method to stimulate current values to a patient is provided, the current values corresponding to brightness values of a digital image to be stimulated to the patient, the method comprising: grouping pixels of the digital image according to brightness values of the pixels, to form groups of pixels with different average brightness values, from lowest brightness to highest brightness; associating at least one electrode brightness group to each group of pixels; and performing a series of stimulations through the electrode brightness groups, wherein a first stimulation is performed by all electrode brightness groups with a first stimulation value, a second stimulation is performed with a second stimulation value higher than the first stimulation value by all electrode brightness groups with exclusion of the electrode brightness group associated to the lowest brightness group of pixels, a third stimulation is performed with a third stimulation value higher than the second stimulation value by all electrode brightness groups with exclusion of the two electrode brightness groups associated to the two lowest brightness groups of pixels, and so on, until a last stimulation performed by the electrode brightness group associated to the highest brightness group of pixels with a stimulation value higher than all previous stimulation values, whereby the electrode brightness group associated to the lowest brightness group of pixels is stimulated for only one stimulation, and the electrode brightness group associated to the highest brightness group of pixels is stimulated for every stimulation.

According to a seventh aspect, a visual prosthesis is provided, the prosthesis comprising a plurality of electrodes adapted to stimulate a patient with current; and a return electrode coupled to the plurality of electrodes and adapted to be placed outside the sclera of the patient, the return electrode having an area $>=55.8$ mm$^2$.

According to an eighth aspect, a visual prosthesis is provided, comprising: an electronics package suitable to be implanted within a human body and to provide a plurality of stimulation signals; an array of electrodes suitable to stimulate visual neurons; a return electrode remote from the visual neurons; means for providing a stimulation signal on at least one of said array of electrodes while providing an opposite signal on said return electrode and at least a second of said array of electrodes.

Further embodiments are provided in the written specification, drawings and claims of the present application.

DETAILED DESCRIPTION

Figure 1:
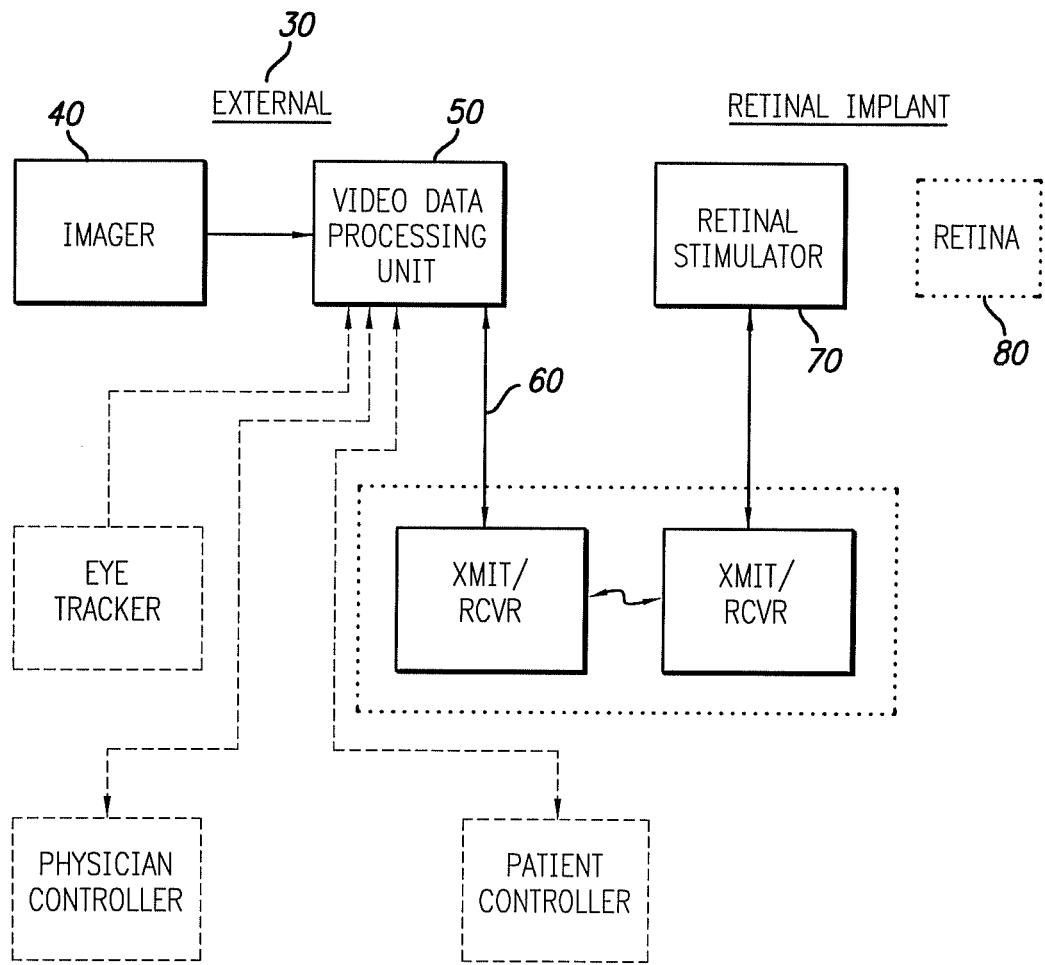
FIG. 1 shows a schematic representation of the main components of a visual prosthesis.

FIG. 1 shows a schematic representation of the main components of a visual prosthesis taken from U.S. published patent application 2005/0288735, incorporated herein by reference in its entirety. In particular, the external portion (30) of the visual prosthesis comprises an imager (40), e.g., a video camera to capture video in real time, and a video data processing unit (50), e.g., comprising a Digital Signal Processor (DSP) to process video data and then send output commands (60) for a retinal stimulator (70) to be implanted on the retina (80) of a patient. The retinal stimulator (70) contains a plurality of electrodes, e.g. 60 electrodes to provide a 6×10 pixel image to the patient, through stimulation of a current whose amplitude corresponds to the brightness of the corresponding pixels.

According to a first embodiment of the present disclosure, discomfort is eliminated through control of timing group assignment. According to such method, for each frame of the video image, the timing groups are actively chosen so that the bright areas of the image are spread across the timing groups, based on the pattern of video levels in the input image.

This method is a variation of the known process of image-based simulation rastering on visual prosthesis implants. According to such process, the electrodes of the retinal stimulator connected to the retina are stimulated at different times. By way of example, if the implant is provided with 60 electrodes and is operating at 30 frames per second, each image frame will last 33 ms. During these 33 ms, the 60 electrodes can be assigned to a certain number of timing groups. The electrodes pertaining to a first group can be stimulated in a first window (e.g., the 0-3 ms interval) inside the 33 ms, the electrodes pertaining to a second group can be stimulated in a second window (e.g., the 3-6 ms interval), and so on.

These groups of electrodes are called "timing groups". The assignment of timing groups (i.e., how many groups, which electrode goes to which group, and so on) is static. In other words, each electrode will be stimulated at a fixed time within each image frame, usually at different amplitudes. Differently from this known technique, the present disclosure provides for an active timing group assignment, meaning that such assignment can be changed with each new image frame.

Figure 2:
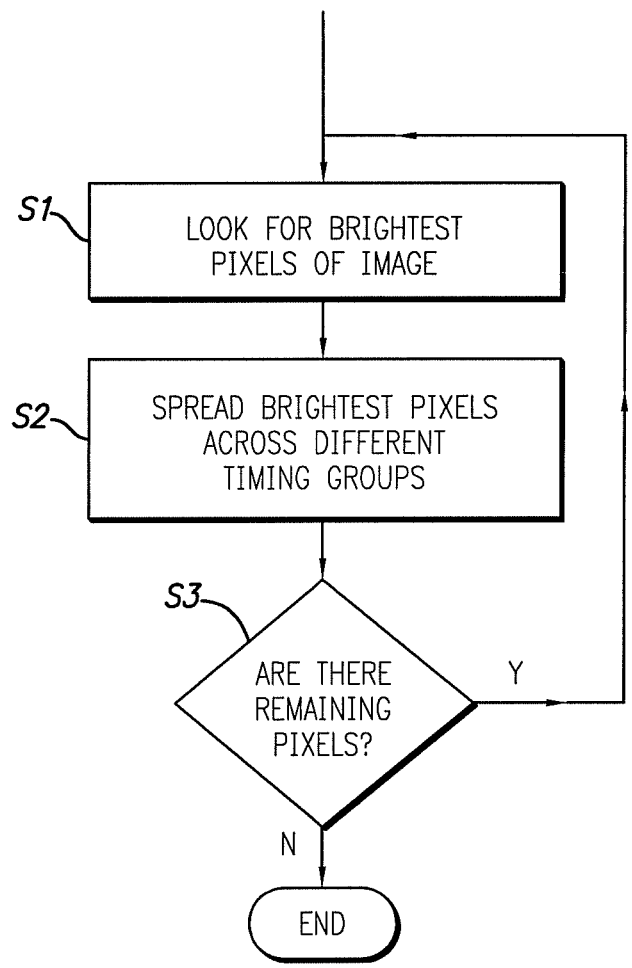
FIG. 2 shows a flow chart related to a first embodiment of the present application.

As mentioned above, the timing groups are actively chosen so that the bright areas of the image are spread into the timing groups. The goal of such method is to reduce the total amount of stimulation current at any instance. In order to do this, each time a new image frame is received, the following steps, also shown in FIG. 2, are performed:
1) looking for the brightest pixels of the image (step S1);
2) spreading the brightest pixels of the image across different timing groups (step S2);
3) repeat the two steps above with the remaining pixels of the image (step S3), and so on.

The total number of timing groups is usually limited by the stimulation frame rate and by hardware bandwidth limitations. Generally speaking, given a stimulation frequency, the total number of timing groups is fixed.

At the end of the method, each timing group will ideally contain an equal amount of brightness. More realistically, the difference in brightness between the various timing groups will be kept at a minimum. The above steps will ensure that the bright areas of an image are evenly spread into the different timing groups. As a consequence, at any instance, the total amount of stimulation power will be substantially the same for each timing group.

According to a further embodiment of the present disclosure, discomfort is eliminated through an edge detection method. As known to the person skilled in the art, common methods of image edge detection often involve computing first or second two-dimensional derivatives in the image brightness value domain. In other words, the more different a pixel is in its brightness value from the other neighboring pixels, the more likely for that pixel to be an "edge." The results are often graded, so that some pixels are more likely to be edges than others. Many standard detection algorithms can be used for such method, such as a Difference-of-Gaussian algorithm, a Difference-of-Laplacian algorithm, and so on.

According to the present disclosure, the total current is analyzed for each frame. In particular, for each frame, the total amount of stimulation current is calculated as the sum of the brightness values at each pixel. Such sum of pixel brightness values can be an instantaneous sum (at instant t), or a sum taken within a small interval (i.e. interval $[t-t_1, t]$ where the order of magnitude of $t_1$ is ms). In case such total current value is above a preset discomfort limit, a possible discomfort for the patient is likely, and action is needed. In particular, such total brightness value should be lowered up to the point that the total current falls just below such discomfort threshold.

In order to reduce the total brightness value on each frame, edge detection and filtering is performed on each frame to decrease the level of stimulation in uniformly bright areas.

Since the edge detection result is graded, a threshold can be used to categorize pixels into "edges" and "non-edges." The lower the threshold chosen, the higher the number of "edge" pixels that will be found.

Figure 3:
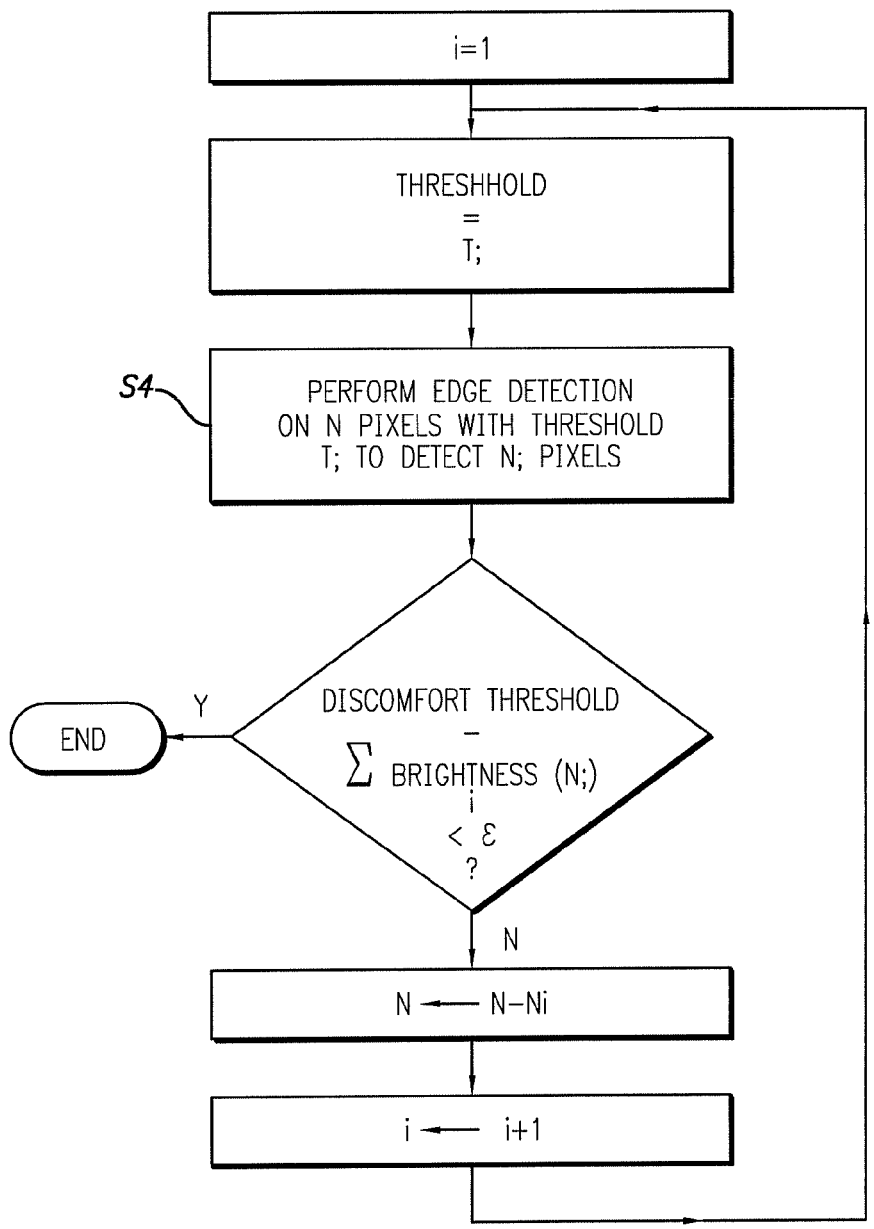
FIG. 3 shows a flow chart related to a second embodiment of the present application.

According to this embodiment, multiple steps of edge detection are performed on each frame, each step having a threshold that is lower than the previous one, as also shown in FIG. 3. Since an edge detection algorithm finds edge pixels as pixels that are different from their neighboring pixels, if the area of interest is uniformly bright, most of the pixels will be equally bright and they will not be detected as edge pixels. Therefore, the number of edge pixels found at each step will be a low number when compared with the total number of pixels analyzed at each step. Assuming that the total number of pixels is N, the first step will be performed on N pixels with a threshold $T_1$ and will provide $N_1$ edge pixels (see step S4 in FIG. 3). The second step will be performed on $(N-N_1)$ pixels with a threshold $T_2 < T_1$ and will provide $N_2$ edge pixels. The third step will be performed on $(N-N_1-N_2)$ pixels with a threshold $T_3 < T_2$ and will provide $N_3$ pixels, and so on. The process will stop at step m when the total current value corresponding to the brightness sum value $N_1+N_2+N_3+\ldots+N_m$, or the integral for i=1 to m of $N_i$, is right under the above mentioned discomfort threshold (see step S5 in FIG. 3).

Therefore, given that the more different a pixel is from the neighboring pixels the more likely such pixel is to represent an important edge, the method explained above allows presentation of the important edges at each frame and guarantees that the total stimulation current does not exceed a preset limit.

According to a further embodiment of the present disclosure, brightness clipping is used to eliminate discomfort. According to this feature, the stimulation levels above a certain value presented to the patient will be saturated to that value. In other words, instead of scaling down high levels of stimulation, this embodiment determines the maximum stimulation possible for each timing group, and saturates the stimulation of this timing group at this level.

Such method can be applied to electrodes pertaining to the same timing group or to all of the electrodes. The goal is to ensure that the total amount of stimulation current is less than a preset limit. For example, the preset limit can be 100 μA for a certain timing group containing electrodes A1, A2, A3, A4 and A5. The respective stimulation amplitudes of such electrodes, according to image information, can be, for example, 10 μA, 5 μA, 25 μA, 35 μA, and 50 μA.

Figure 4:
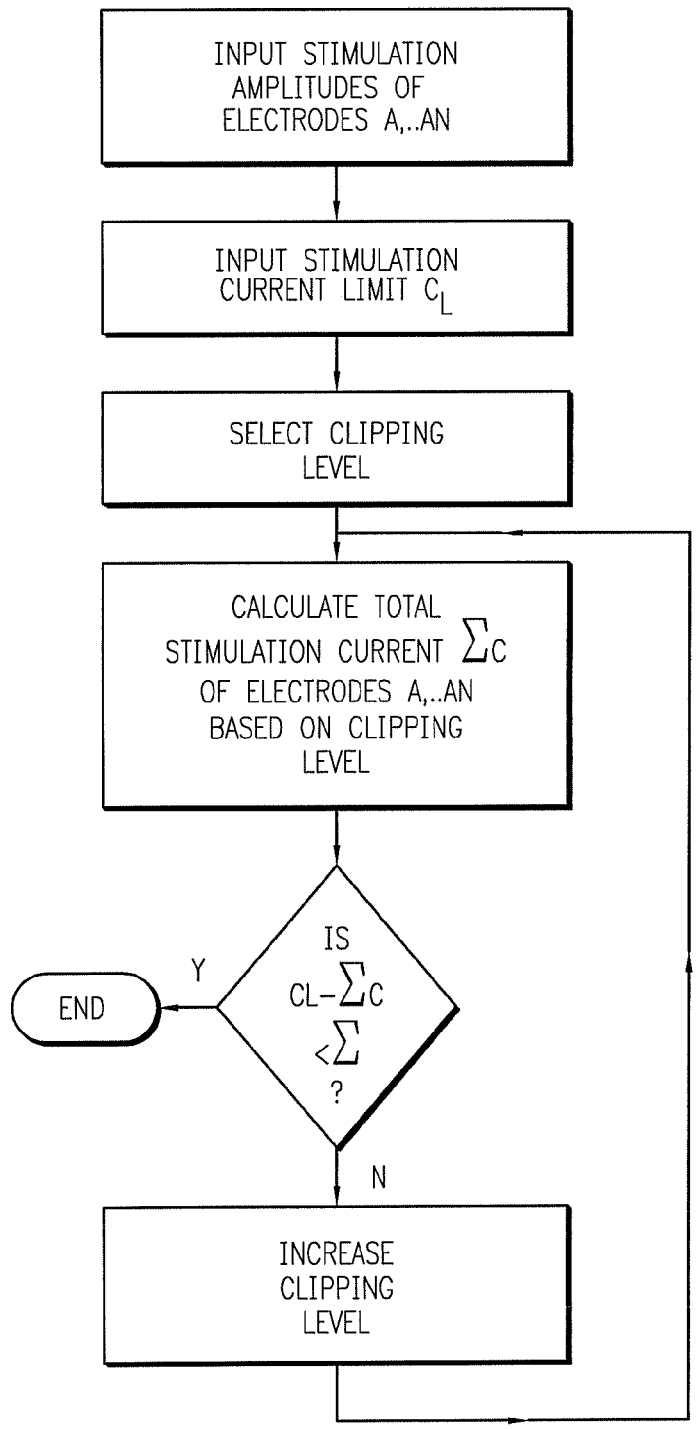
FIG. 4 shows a flow chart related to a third embodiment of the present application.

Once brightness clipping is applied, a clipping level is initially selected. For example, if such clipping level is 15 μA, A1 and A2 (10 μA and 5 μA, respectively) will not be clipped, while A3, A4 and A5 (25 μA, 35 μA, and 50 μA, respectively) will be clipped to 15 μA, thus producing a total current amount of 60 μA. On the other hand, if the clipping level is 25 μA, only A4 and A5 will be clipped to that value, for a total current amount of 90 μA. Further, if the clipping level is set to 35 μA, only A5 will be clipped, for a total current amount of 110 μA. Given that the preset limit in this example is 100 μA, the clipping level guaranteeing the highest total current amount under that limit is 25 μA. Therefore, a clipping level of 25 to is chosen. FIG. 4 shows a flow chart illustrating a possible implementation of such embodiment.

Such method will be applied on every image frame.

A further embodiment of the present disclosure will now be shown. According to this embodiment, direct reduction of the current is obtained by scaling it down by a factor which is dependent on the sum of the current in all electrodes (i.e. the total brightness of the frame). In particular, a look-up table (LUT) is implemented, that continuously scales down or up the stimulation amplitude of single electrodes according to such overall stimulation level. Hence, the current of a specific electrode is a function of the brightness in the corresponding video area and of the total brightness in the acquired image (as determined by the LUT).

Figure 5:
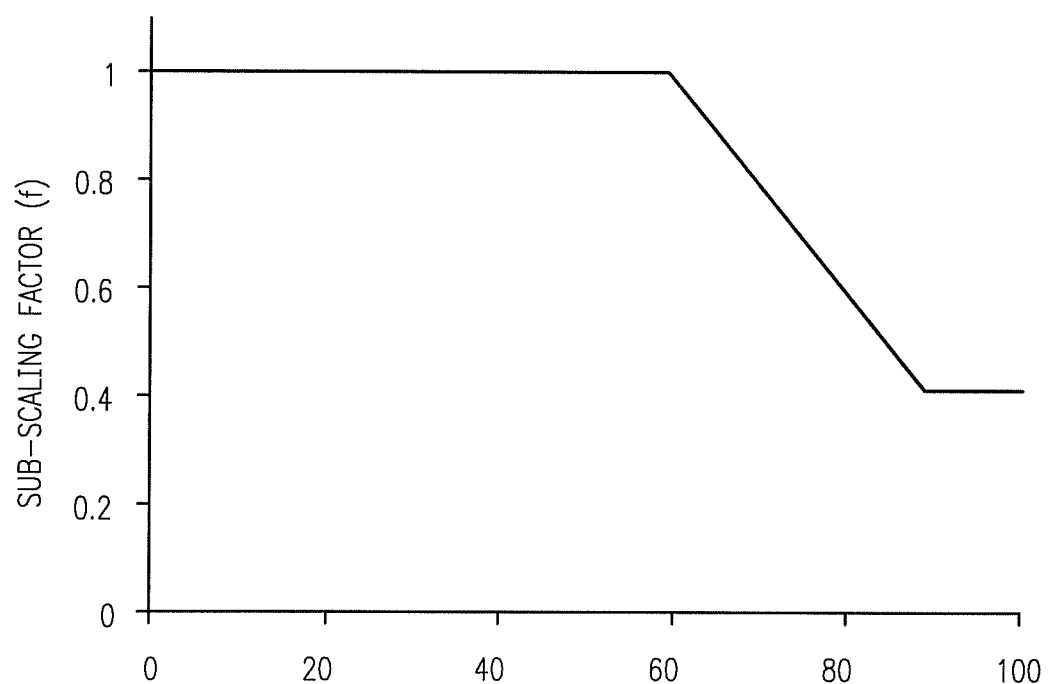
FIG. 5 shows a look-up table diagram related to a fourth embodiment of the present application.

In other words, for each frame the total brightness level will be calculated and the current stimulation level on each electrode will be scaled down in order to maintain a relatively fixed current summation value. FIG. 5 shows an example of the brightness scaling look-up table of an electrode. As shown in this exemplary table, if the total current is up to 60 μA, no scaling occurs. When the current goes from 60 μA to 90 μA, liner scaling occurs from 100% to 40%. When the total current is 90 μA or more, the current stimulation level on the electrode has a 40% scaling level, i.e. it is multiplied by 0.4.

It should be noted that such feature will set a different maximum current for each electrode for different images, thus effectively increasing the dynamic range of the visual prosthesis and providing a brighter percept for images with objects that cover only a small portion of the field of view (i.e., only few electrodes will be stimulated, with minimal scaling).

According to a further embodiment of the present disclosure, an arrangement is further provided to compensate for the interactions between electrodes so that images or patterns can be presented with more consistent contrast and brightness, and discomfort to the patient can be eliminated. In particular, the image signal is processed before being sent to the retinal stimulator including the electrodes (see stimulator (70) shown in FIG. 1), as shown in FIG. 6.

Figure 6:
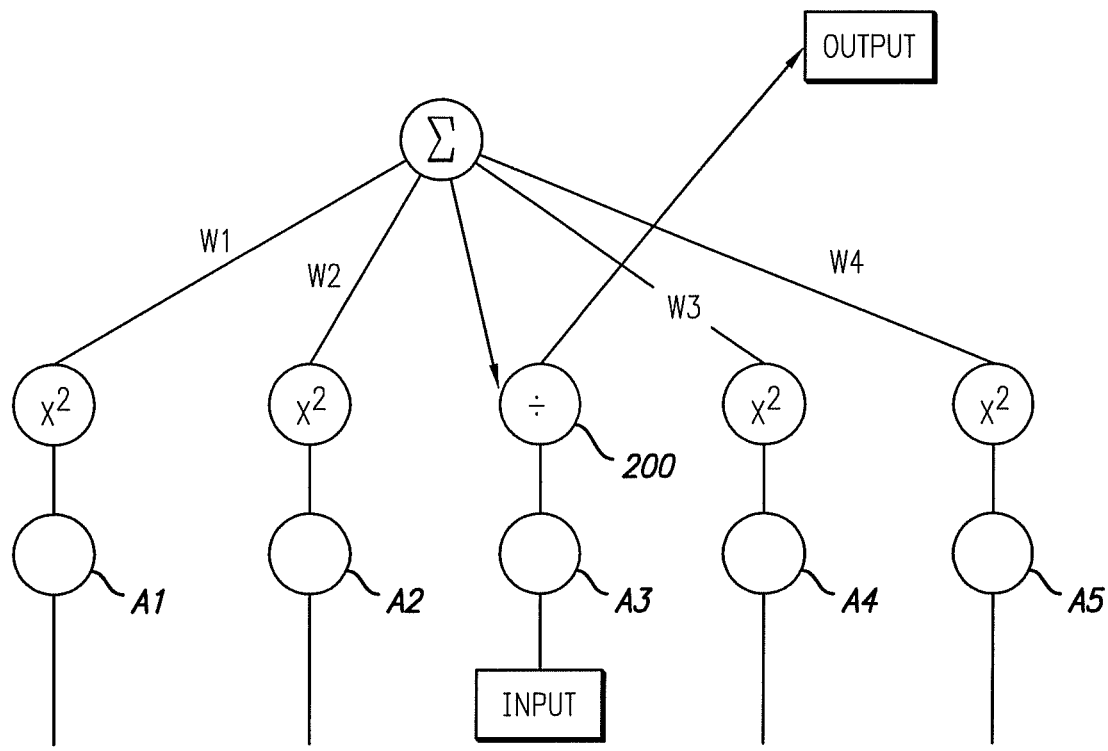
FIG. 6 shows a schematic diagram of a further embodiment of the present disclosure.

FIG. 6 shows the brightness levels A1, A2, A3, A4, A5 before being sent to the respective electrodes of the retinal stimulator. According to this further embodiment, each brightness level, e.g., A3, is divided (200) by the weighted sum of the unprocessed brightness levels on the surrounding electrodes (i.e. electrodes or pixels in the spatial neighborhood of the electrode at issue) raised to an exponent, e.g., 2. For examples, assuming that electrodes 1, 2, 4 and 5 surround electrode 3, the amount by which A3 will be divided is:

$$W1*(A1)^2+W2*(A2)^2+W4*(A4)^2+W5*(A5)^2$$

The specific weights W1, W2, W4, W5 can be determined through psychophysical experiments using, for example, the notion of divisive normalization, where the weights are directly related to the distance. In other words, the closer a pixel is to another, the higher its weight and thus the more it contributes to the divisive normalization step. Reference can be made to Carandini M, Heeger D J, *Summation and Division by Neurons in Primate Visual Cortex, Science* (1994), May 27; 264(5163):1333-6, incorporated herein by reference in its entirety.

The present disclosure further provides for a stimulation method that takes advantage of the current summation effect and decreases the total stimulation current. In particular, according to the current summation principle, if multiple electrodes are stimulated together (i.e., the electrodes are in the same timing group), the minimum current needed to stimulate each electrode for light perception is generally lower than the minimum current needed to stimulate an electrode if such electrode were stimulated alone (individual electrode threshold).

According to the present disclosure, the input image pixels are first grouped based on their brightness values. For example, the M pixels can be grouped in N different pixel groups, where group 1 contains pixels M1, group 2 contains pixels M2, and so on until group N, which contains pixels MN, where M1+M2+ . . . +MN=M. Pixels M1 will be the dimmest pixels of the image, pixels M2 will be brighter than pixels M1, and so on, until pixels MN, which are the brightest pixels of the image.

Therefore, N different timing groups will be formed. A first timing group will contain electrodes associated with pixels M1, a second timing group will contain electrodes associated with pixels M2, and so on, up to an Nth timing group containing electrodes associated with pixels MN. Alternative forms of brightness segmentation or methods like histogramming may also be adopted.

These N timing groups will be stimulated in N steps, as follows.

The first stimulation step will stimulate group 1 (associated to pixels M1 with the lowest brightness value) and all other electrodes associated to pixels having equal or higher brightness values. As a consequence, the first stimulation step will stimulate all groups 1 . . . N. The stimulation amplitude of all groups 1 . . . N will be the same and will be determined by the lowest brightness value of pixels M1.

The second stimulation step will stimulate group 2 (associated to pixels M2 having brightness values higher than pixels M2 but lower than pixels M3) and all other electrodes associated to pixels having equal or higher brightness values. As a consequence, the second stimulation step will stimulate all groups 2 . . . N. The stimulation amplitude of all groups 2 . . . N will be the same and will be determined by the lowest brightness value of pixels M2.

The third, fourth, etc stimulation steps will proceed similarly, until the Nth step is reached, where only group N electrodes (associated to pixels MN having the brightest values) will be stimulated. The stimulation amplitude of group N will be determined by the brightness value of pixels MN.

Therefore, for groups with different brightness values, different stimulation amplitudes are used.

Figure 7:
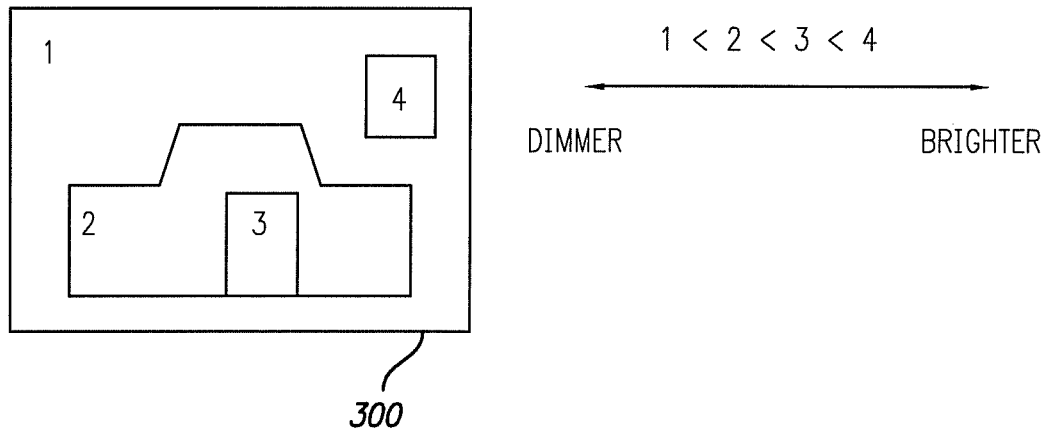
FIG. 7 shows a digital image divided into brightness groups.
Figure 8:
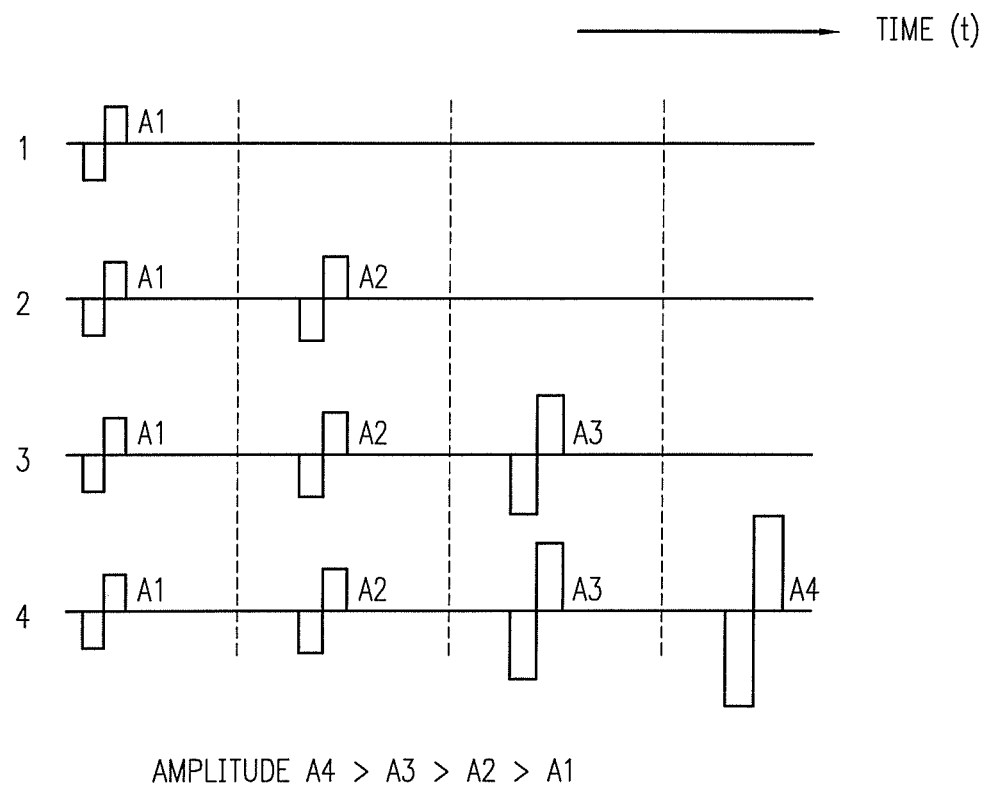
FIG. 8 shows a stimulation timing diagram based on the embodiment of FIG. 7.

FIGS. 7 and 8 show an exemplary embodiment of the present disclosure based on the above paragraphs. As shown in FIG. 7, input image (300) is separated into 4 different brightness groups. Group 1 is the dimmest group and group 4 is the brightest. FIG. 8 shows a timing diagram, where line 1 relates to the stimulation time and amplitude of the electrodes of brightness group 1, line 2 relates to the stimulation time and amplitude of the electrodes of brightness group 2, and so on. As shown in FIG. 8, all electrodes (brightness group 1+brightness group 2+brightness group 3+brightness group 4) are stimulated together at the first time slot with amplitude A1. With the presence of current summation, this will provide a dim background. In the next time slot, brightness groups 2, 3 and 4 are stimulated together at amplitude A2, and provide an increased brightness value for group 2. This stimulation scheme continues until all brightness groups are stimulated.

As shown in FIG. 8, from a single group point of view, the modulated amplitudes can provide a more persistent perception. For example, group 4 will be stimulated with a train of pulses with increasing amplitudes over time.

As already mentioned above, the embodiment according to the above paragraphs takes advantage of the current summation effect and will reduce the total amount of stimulation power needed. In other words, any of the amplitudes A1 of FIG. 8 can be significantly less than the individual electrode perception threshold.

Moreover, for any brightness group, if the total stimulation current exceeds certain safety limits, multiple timing groups can be used to separate the stimulation current. In other words, the current can be spread out temporally.

The embodiment according to the above paragraphs can be applied to both the brightness (i.e. video stimulation) and current (i.e. direct stimulation) domain.

A further technique for reducing discomfort is related to the dimensions of the return electrode during stimulation.

Figure 9:
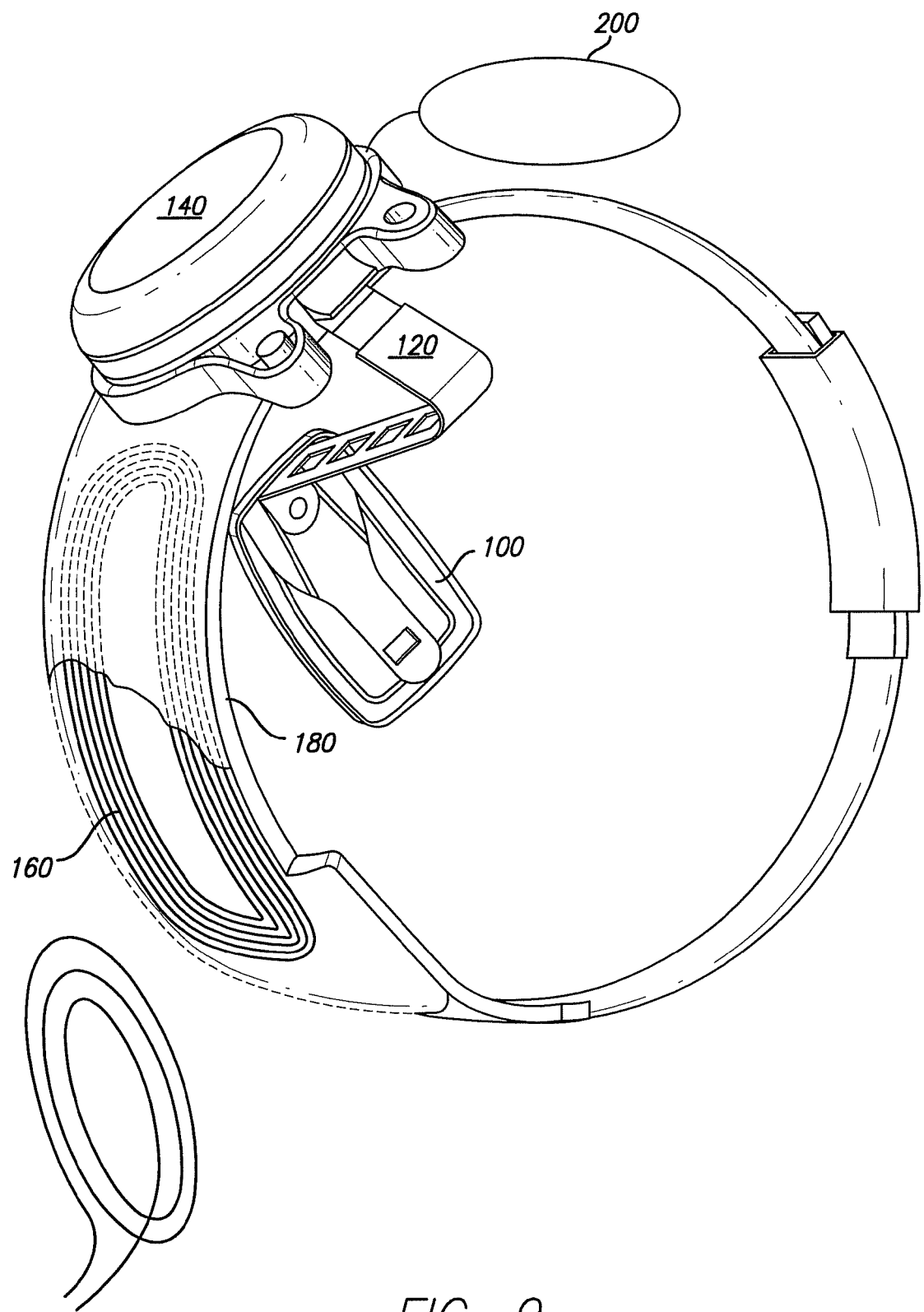
FIG. 9 shows a retinal prosthesis.
Figure 10:
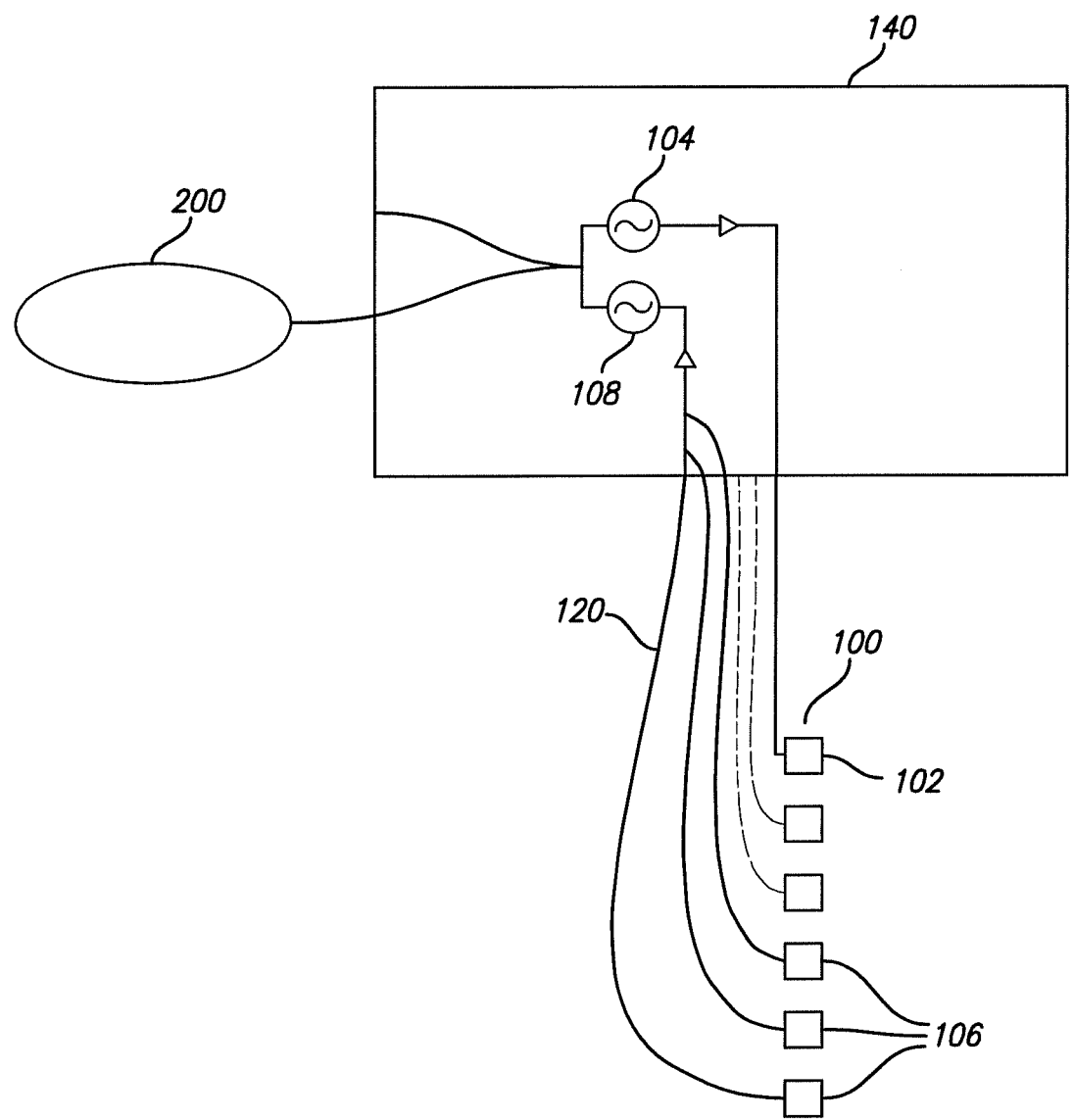
FIG. 10 shows an electrical schematic of the preferred embodiment.

FIG. 9 shows a perspective view of the implanted portion of a preferred retinal prosthesis adapted to be used will any one of the embodiments of the present disclosure. A flexible circuit includes a flexible circuit electrode array 100 which is mounted by a retinal tack (not shown) or similar means to the epiretinal surface. The flexible circuit electrode array 100 is electrically coupled by a flexible circuit cable 120, which pierces the sclera and is electrically coupled to an electronics package 140, external to the sclera. The electronics package 140 is electrically coupled to a secondary inductive coil 160. Preferably the secondary inductive coil 160 is made from wound wire. Alternatively, the secondary inductive coil 160 may be made from a flexible circuit polymer sandwich with wire traces deposited between layers of flexible circuit polymer. The secondary inductive coil receives power and data from a primary inductive coil 170, which is external to the body. The electronics package 140 and secondary inductive coil 160 are held together by a molded body 180. The molded body 180 holds the electronics package 140 and secondary inductive coil 160 end to end. The secondary inductive coil 160 is placed around the electronics package 140 in the molded body 180. The molded body 180 holds the secondary inductive coil 160 and electronics package 140 in the end to end orientation and minimizes the thickness or height above the sclera of the entire device. In the embodiment of FIG. 9, the electronics package 140 acts as a return electrode.

According to an embodiment of the present disclosure, Applicants have optimized the dimensions of the return electrode to minimize discomfort to a subject wearing the retinal prosthesis.

It can be assumed that a maximum current output for the return electrode 200 is 3 mA and a maximum pulse width for the stimulating current on the return electrode is 3.1 ms. In case of a niobium (Nb) electrode, the charge capacity is 50 $\mu C/cm^2$. For a safe stimulation, under the above maximum conditions, the charge density on the Nb return electrode should be smaller than the Nb electrode charge capacity. In other words, $$(3000 \ \mu A * 3.1 * 0.001 \ s)/\text{Area} <= 50 \ \mu C/cm^2$$

It follows that Area $>=18.6$ mm$^2$. Adding a three times safety margin, the Applicants have noted that Area $>=55.8$ mm$^2$.

A further condition that can be imposed on the return electrode is a ratio between the area of the return electrode and the total area of the stimulating electrodes. In particular, the area of the return electrode should be 100 times larger than the total area of the stimulating electrodes. Assuming 30 electrodes firing at the same phase, Applicants have calculated the total area of the stimulating electrodes to be 0.94 mm$^2$. Therefore, the further condition that can be imposed on the return electrode is $$\text{Ret electrode area/Stim electrodes area} >= 100 \rightarrow$$
$$\text{Ret electrode area} >= 94 \ mm^2$$

Another embodiment of the present disclosure relates to pseudo-multi-polar stimulation. In true multi-polar stimulation, two or more stimulating electrodes are driven with opposite charge to reduce discomfort in a subject, resulting in a net zero charge. In its simplest form, two electrodes are driven with equal and opposite charge, creating a percept at each electrode. However, there are several problems with true multi-polar stimulation. First, multi-polar stimulation is inefficient, as some power is transferred through saline along the electrode array surface. Also, if percepts are produced at each pole, the image must be analyzed for the desired multiple percepts before stimulation. This is further complicated by the fact that cathodic stimulation is more efficient than anodic stimulation. In other words, with equal and opposite charge, the cathodic electrode will create a brighter percept. Nevertheless, the net charge on each electrode must be balanced with a biphasic pulse.

In accordance with an embodiment of the present disclosure, discomfort is reduced by way of pseudo-multi-polar stimulation, where a remote return electrode and a current stimulating electrode are provided see, for example, remote electrode 200 shown in FIG. 9 described above. According to this embodiment, one or more currently unused stimulating electrodes are held common to the remote return electrode, and thereby, used as additional return electrodes. Preferably, the additional return electrodes are geographically remote from the stimulating electrode to minimize power loss along the electrode array surface. A biphasic pulse should be used to provide a net charge of zero on each electrode.

By using one more stimulating electrodes as additional return electrodes in accordance with the above, each stimulating electrode acting as return electrode may be kept below the threshold of stimulation for that electrode. This allows for a smaller remote return electrode (e.g., electronics package) for a given device power without creating a percept on the return electrode.

The present disclosure can be used in any retinal stimulation system and cortical visual prostheses.

The person skilled in the art will also understand that while each of the embodiments discussed above can be applied alone, they can also be applied in combination.

Accordingly, what has been shown are image processing techniques and functional electrical stimulation to eliminate discomfort during electrical stimulation of the retina. While these techniques have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

The invention claimed is:

1. A method for assigning image pixels of a digital image to electrodes of a visual prosthesis, the electrodes adapted to provide electrical signals to a patient according to a temporal stimulation pattern, the temporal stimulation pattern defining one or more timing groups of electrodes, the method comprising:
   a) providing an image source and a video processing unit;
   b) sending a digital image from said image source to said video processing unit;
   c) selecting a group of brightest pixels of the digital image in the video processing unit;
   d) selecting a group of remaining pixels, not in said group of brightest pixels;
   e) dividing the digital image into timing groups;
   f) spreading said group of brightest pixels across more than one of said timing groups;
   g) repeating a) and b) for said group of remaining pixels of the image, until all pixels have been assigned to said one or more timing groups; and
   h) stimulating visual neurons to induce said digital image by stimulating pixels in different timing groups at different times.

2. The method of claim 1, wherein the digital image is a digital video frame of a digital video signal having a plurality of digital video frames.

3. The method of claim 1, said method being a method for reducing discomfort to a patient wearing the visual prosthesis.

4. A method for reducing discomfort to a patient wearing a visual prosthesis, the visual prosthesis comprising a plurality of electrodes adapted to stimulate the patient with current, wherein an amount of current to be provided by each electrode is indicative of brightness of an image area associated to said each electrode, the method comprising:
   providing an image source and a video processing unit;
   sending a digital image from said image source to said video processing unit;
   scaling the amount of current to be provided by said each electrode according to a scaling factor in the video processing unit, the scaling factor depending on a predetermined maximum and a sum of the amount of current to be provided by all electrodes;
stimulating visual neurons to induce said digital image with signals adjusted by said scaling factor.

5. The method of claim 4, wherein the scaling occurs by way of a look-up table.

6. The method of claim 4, wherein no scaling is applied if the sum of the amount of current to be provided by all electrodes is less than a discomfort level for the patient.

\* \* \* \* \*